United States Patent [19]
Coombs et al.

[11] 3,959,308

[45] May 25, 1976

[54] SUBSTITUTED NAPHTHO PYRAZOLES

[75] Inventors: Robert V. Coombs, Chatham; William J. Houlihan, Mountain Lakes, both of N.J.

[73] Assignee: Sandoz, Inc., E. Hanover, N.J.

[22] Filed: June 27, 1974

[21] Appl. No.: 483,625

Related U.S. Application Data

[62] Division of Ser. No. 333,557, Feb. 20, 1973, Pat. No. 3,843,664.

[52] U.S. Cl. .................... 260/310 R; 260/310 C; 260/296 T

[51] Int. Cl.² .................................. C07D 231/54

[58] Field of Search ..................... 260/310 R, 296 T

[56] References Cited
UNITED STATES PATENTS 3,842,088   10/1974   Habeck et al. ................. 260/310 R

*Primary Examiner*—Donald B. Moyer
*Attorney, Agent, or Firm*—Gerald D. Sharkin; Robert S. Honor; Thomas O. McGovern

[57] ABSTRACT

Substituted naphtho [1,2-c] pyrazoles, e.g., 3-(4-pyridyl)-2H-naphtho[1,2-c]-pyrazole, are useful as non-estrogenic anti-fertility agents.

3 Claims, No Drawings

SUBSTITUTED NAPHTHO PYRAZOLES

This is a division of application Ser. No. 333,557 filed Feb. 20, 1973 which issued as U.S. Pat. No. 3,843,664 on Oct. 22, 1974.

This invention relates to naphtho [1,2-c] pyrazole derivatives. More particularly it relates to 3-aryl and 3-heterocyclic derivatives of naphtho [1,2-c]pyrazole and their use in pharmaceutical compositions.

The compounds of this invention may be represented by the following formula:

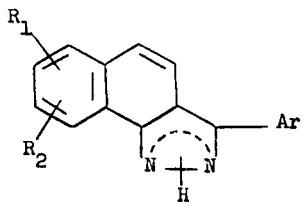

(I)

where Ar is

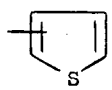 ,  ,  or 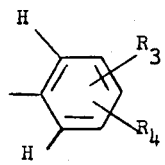

and
$R_1$, $R_2$, $R_3$ and $R_4$ each independently represent hydrogen, halo having an atomic weight of about 19 to 36, lower alkyl, i.e., alkyl having 1 to 4 carbon atoms, e.g., methyl, ethyl, isopropyl and the like; lower alkoxy, i.e., alkoxy having 1 to 4 carbon atoms, e.g., methoxy, ethoxy, isopropoxy and the like, or trifluoromethyl or
$R_1$ and $R_2$ or $R_3$ and $R_4$ together independently represent methylenedioxy attached to adjacent carbon atoms, provided that when $R_1$ and $R_2$ or $R_3$ and $R_4$ are independently trifluoromethyl or tertiary butyl, they are on other than adjacent carbon atoms, and pharmaceutically acceptable acid addition salts thereof.

The pyrazole ring (A) in the compounds of formula (I) can have the following structures

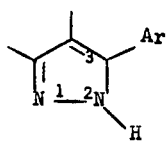 or 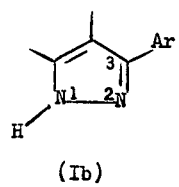

(Ia)          (Ib)

It should be noted that the compounds of structures (Ia) and (Ib) are considered equivalent in the art and are known to exist in both tautomeric forms.

The compounds of formulas (I) can be prepared by the following reaction scheme:

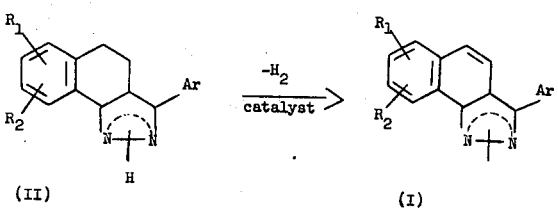

where $R_1$, $R_2$, Ar and the proviso are as set out above.

The compounds of formula (I) are prepared by dehydrogenating a compound of formula (II) in the presence of a noble metal dehydrogenation catalyst. The particular noble metal catalyst used is not critical, but platinum or palladium, either alone or supported on carbon, alumina, talc, and the like is preferred, and 5% palladium on carbon is especially preferred.

Although a solvent is not required, it is preferred that the reaction be carried out in the presence of an inert solvent such as the lower alkanols having 1 to 4 carbon atoms, aliphatic or aromatic hydrocarbons, halogenated hydrocarbons, straight chain ethers or cyclic ethers. The particular solvent used is not critical, but the lower alkanols, such as methanol, ethanol and butanol and/or dioxane are preferred. The temperature of the reaction also is not critical, but it is generally carried out between 50° and 200°C preferably at the reflux temperature of the system. It is also preferred that the reaction be run for from 48 hours to 5 days. The product is recovered in the usual manner, e.g., by evaporation and crystallization.

The compounds of formulas (I) may also be prepared by the following reaction scheme:

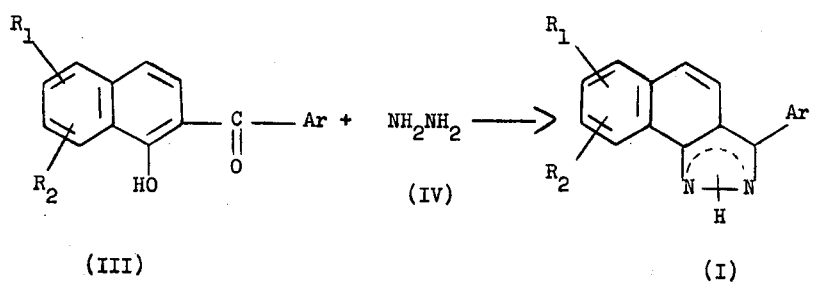

where $R_1$, $R_2$, Ar and the proviso are as set out above.

The compounds of formula (I) are prepared by refluxing a compound of the formula (III) with a hydrazine of formula (IV) in diethylene glycol. It is preferred that the reaction be run for from about 1 to 8 hours and that it be carried out under an inert atmosphere e.g. nitrogen argon, helium and the like. The product is isolated by standard techniques, e.g., recrystallization.

The compounds of formula (I) may also be prepared in accordance with the following reaction scheme:

where $R_1$, $R_2$, Ar and the proviso are as defined above.

The compounds of formula (II) are prepared by treating a compound of formula (VI) with hydrazine of formula (IV). The reaction is preferably carried out under acidic catalysis which can be provided by a mineral acid such as hydrochloric acid, sulfuric acid, and the like, an organic acid such as p-toluenesulfonic or acetic acid or a Lewis acid such as boron trifluoride. The preferred acids are p-toluenesulfonic acid and boron trifluoride. Although a solvent is not required, it

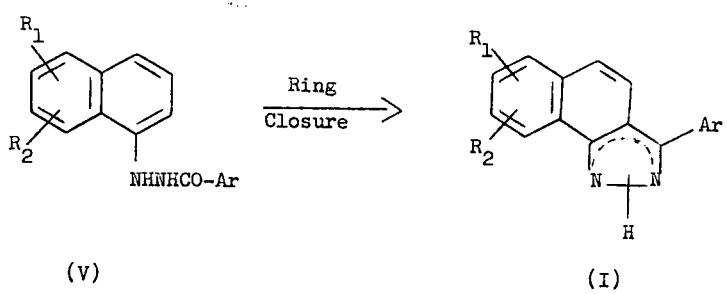

where $R_1$, $R_2$, Ar and the proviso are as defined previously.

The compounds of formula (I) are prepared by ring closure of a compound of formula (V) with phosphorous oxychloride or phosphorus pentachloride in an inert solvent. Although the particular solvent used in the reaction is not critical, the preferred solvents are aromatic hydrocarbons such as benzene, toluene, xylene and the like or excess phosphorus oxychloride or pentachloride. The temperature at which the reaction is carried out is not critical, but it is preferred that the reaction be run at about 50° to 200°C especially at the reflux temperature of the system. The time also is not critical, but it is preferred that the reaction be run for from 10 to 24 hours. The product is recovered by conventional techniques, for example, recrystallization.

The compounds of formula (II) are prepared according to the following procedure:

is preferred that the reaction be carried out in the presence of an inert solvent such as the lower alkanols having 1 to 4 carbon atoms, aliphatic or aromatic hydrocarbons, halogenated hydrocarbons, straight chain ethers or cyclic ethers. The particular solvent used is not critical, but the lower alkanols, such as methanol, ethanol or butanol or dioxane are preferred. The temperature of the reaction also is not critical, but it is generally carried out between 35° and 200°C, preferably at the reflux temperature of the system. For optimum results it is preferred that the reaction be run for from 8 hours to 5 days. The product is recovered in the usual manner, e.g., by evaporation and crystallization.

The compounds of formula (V) can be prepared according to the following reaction scheme:

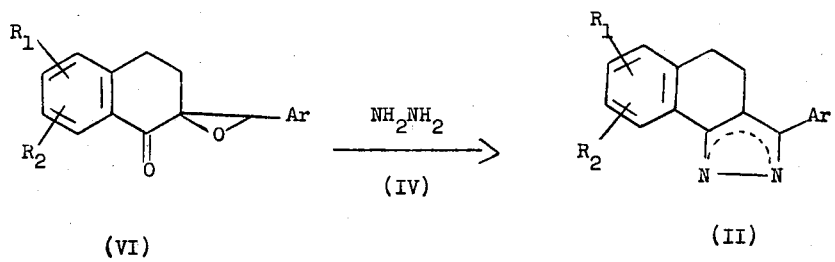

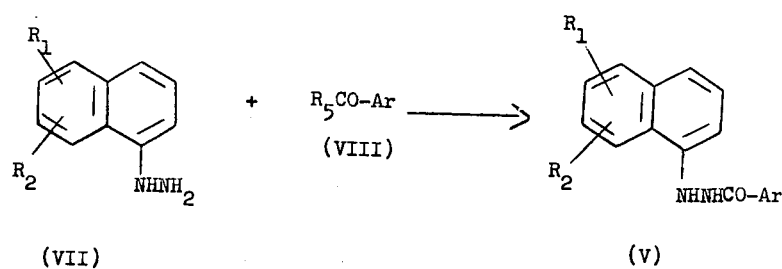

where
R₅ is halo having an atomic weight of about 35 to 80 or lower alkoxy as defined above and
R₁, R₂, Ar and the proviso are as set out above.

The compounds of formula (V) are prepared by treating a compound of formula (VII) with a compound of formula (VIII). Although a solvent is not necessary, it is preferred that the reaction be carried out in an inert solvent such as lower alkanols having 1 to 4 carbon atoms aliphatic or aromatic hydrocarbons, halogenated hydrocarbons, straight chain or cyclic ethers or excess compound of formula (VIII). The particular solvent used is not critical, but the preferred solvents are the lower alkanols such as methanol, ethanol, butanol and the like. The temperature of the reaction is not critical, but it is normally carried out between 35° and 150°C, preferably at the reflux temperature of the system. It is also preferred that the reaction be run for from 5 to 48 hours. The product is recovered by conventional techniques, e.g., evaporation.

The compounds of formula (VI) are prepared in accordance with the following reaction scheme:

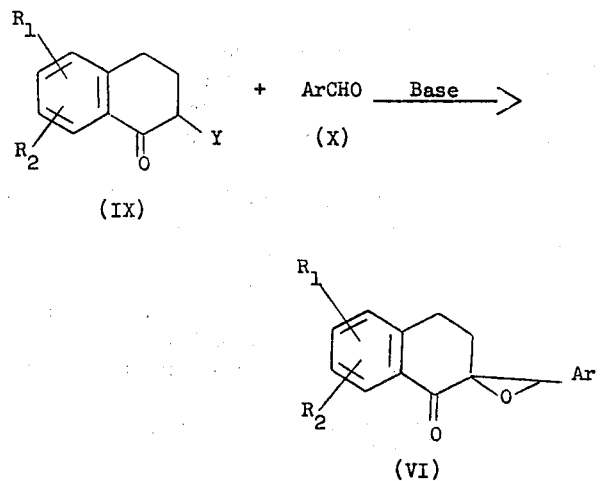

where
Y is a leaving group and
R₁, R₂, Ar and the proviso are as set out above.

The compounds of formula (VI) are prepared by treating the compounds of formula (IX) with the compounds of formula (X) under basic conditions in an inert solvent. It is preferred that the reaction be run in an inert atmosphere such as argon, helium and especially nitrogen. The leaving group Y in formula (IX) can be any of the conventional leaving groups employed in such a reaction such as chlorine, bromine, iodine, tosylate, mesylate and the like. The preferred leaving group is the halogens, especially chlorine or bromine. The basic conditions for the reaction are provided by alkali or alkali earth metal hydroxides, alkali metal lower alkoxides, tertiary aliphatic and aromatic amines and tertiary cyclic amines such as pyridine and the like. Although the particular solvent used is not critical, the lower alkanols having 1 to 4 carbon atoms such as methanol, ethanol, butanol and the like are especially preferred, in particular the lower alkanol corresponding to the alkali metal alkoxide when used. The temperature of the reaction is not critical, but is is generally carried out between 0° and 30°C, preferably about 5° to 10°C. Although the time is not critical, it is preferred that the reaction be run for from 1 to 5 hours. The product is recovered by standard techniques e.g., by crystallization or distillation.

The compounds of formula (IX) are prepared by well known procedures from compounds of the formula:

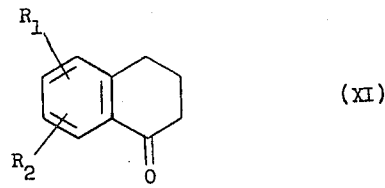

where R₁, R₂ and the proviso are as set out above.

The compounds of formula (IX) may be obtained by standard procedures from compounds of formula (XI). For example, the chlorine or bromine substituted compounds can be prepared by treating the compound of formula (XI) with chlorine or bromine, preferably in an inert solvent such as acetic acid, chloroform or carbon tetrachloride. The reaction can be carried out at temperatures from room temperature to 50° over a period of 1 to 12 hours, preferably 3 to 6 hours. The particular solvent, temperature or time used in the reaction are not critical.

The tosylate and mestylate can be prepared from the chlorine or bromine substituted compound by treatment with a tosylate or mesylate salt, such as sodium or potassium tosylate or mesylate in an inert solvent such as lower alcohols, toluene or benzene. The reaction is preferably carried out at temperatures between 15° to 70° especially between 25° to 40° for a period of 2 to 10 hours, preferably 4 to 7 hours. The particular solvent used, the temperature and the time of the reaction are not critical.

The hydrazine of formula (IV) and many of the compounds of formula (III), (VII), (VIII), (X) and (XI) are known and are prepared by procedures disclosed in the literature. The compounds of formula (III), (VII), (VIII), (X) and (XI) not specifically disclosed in the literature may be prepared by analgous methods using known starting materials.

The compounds of formula (I) are useful because they possess pharmacological activity in animals. In particular, the compounds are useful as anti-fertility agents as indicated by their activity in female Wistar rats which are injected daily with 2 mg. of the compound for eight successive days starting on the day of vaginal cornification. At the time of the 4th injection, males of known fertility are cohabitated with the females (one female with one male) until the end of the treatment period. The males are separated from the females 24 hours following the last injection. The females are sacrificed 6 days later, and examined for the presence or absence of implantation sites.

The use of the compounds as anti-fertility agents is further indicated by their luteolytic properties which results in the compounds being abortifacient agents. The luteolytic activity is determined using pseudopregnant rabbits treated with corn oil or compound of formula (I) (1–100 mg per day) suspended in corn oil on days 3 through 8 of pseudopregnancy. Blood samples are obtained daily throughout the length of pseudopregnancy. Plasma samples are analyzed for progestin content according to the method of Johansson et. al. (Endocrinology 82, 143, 1968). The compound is judged active if plasma progestin levels are similar to pretreatment values on day 12 of pseudopregnancy.

Abortifacient activity is also determined in female proestrous rats (Royal Hart, Wistar strain) selected from a colony and caged with fertile males. On the following day, pregnancy is confirmed by the presence of spermatozoa in the vaginal smear. On the seventh day following mating, the females are treated with 1 to 30 milligrams of the compound to be tested. The animals are injected daily for a total of 7 days; and on the eighth day following the first injection, the animals are killed and the uterus checked for the presence of absence of implantation sites.

The compounds of formula (I), when used as anti-fertility agents, exhibit none of the estrogenic effects and side effects exhibited by the steroidal type compounds used for these purposes.

When the compounds are employed for the above utility, they may be combined with one or more pharmaceutically acceptable carriers or adjuvants, and may be administered orally in such forms as tablets, capsules, elixirs, suspensions and the like, e.g., bucally or sub-lingually as a tablet, parenterally in the form of an injectable solution or suspension or in special forms such as suppositories, e.g., vaginal inserts, pessaries, and the like. Depending upon the compound employed and the mode of administration the exact dosage utilized may vary.

Furthermore, the compounds of formula (I) may be similarly administered in the form of their non-toxic pharmacautically acceptable acid addition salts. Such salts possess the same order of activity as the free base, are readily prepared by reacting the base with an appropriate acid and accordingly, are included within the scope of the invention. Representative of the acid addition salts are the mineral acid salts, such as the hydrochloride, hydrobromide, sulfate, phosphate and the like and the organic acid salts, such as the succinate, benzoate, acetate, p-toluenesulfonate, benzenesulfonate, and the like.

In general, satisfactory results are obtained when the compounds of formula (I) are administered as anti-fertility agents at a daily dosage of about 1.0 milligrams to about 200 milligrams orally, subcutaneously or intramuscularly per kilogram of animal body weight. This daily dosage is preferably administered 1 to 4 times a day or in sustained release form. For most large mannals, such as primates, the total daily dosage is from about 1 milligram to about 600 milligrams. Dosage forms suitable for internal use comprise from about 0.25 milligrams to about 300 milligrams of the active compound in intimate admixture with a solid or liquid pharmaceutically acceptable carrier or diluent.

A representative formulation suitable for intramuscular administration once a day in fertility control is an injectable suspension prepared by standard techniques which contain the following:

| Ingredients | Weight (mg) |
| --- | --- |
| 3-(4-pyridyl)-2H-naphtho[1,2-c]pyrazole | 200 |
| sodium carboxy methyl cellulose U.S.P. | 1.25 |
| methyl cellulose | 0.4 |
| polyvinylpyrrolidone | 5 |
| lecithin | 3 |
| benzyl alcohol | 0.01 |
| buffer agent to adjust pH for desired stability | q.s. |
| water | for injection q.s. to 2 ml. |

EXAMPLE 1

3-(4-pyridyl)-2H-naphtho[1,2-c]pyrazole

Step A: 3'-(4-pyridyl)-spiro[1,2,3,4 tetrahydronaphthalene-2,2'-oxirane]-1-one.

To a stirred solution of 11.3 g of 2-bromo-α-tetralone and 5.5 g. of pyridine-4-carboxyaldehyde in 20 ml. of methanol under nitrogen is added at 5° to 10°C a solution of sodium methoxide in methanol (prepared by dissolving 1.15 g. of sodium in 50 ml. methanol). After 2 hours, 3'-(4-pyridyl)-spiro[1,2,3,4-tetrahydronaphthalene-2,2'-oxirane]-1-one precipitates and is filtered off and recrystallized form methanol (m.p. 180°-182°C).

When an equivalent amount of
a. 2-bromo-6-chloro-α-tetralone;
b. 2-bromo-6-methyl-α-tetralone;
c. 2-bromo-6,7-dimethoxy-α-tetralone;
d. 2-bromo-6-trifluoromethyl-α-tetralone or
e. 2-bromo-6,7-methylenedioxy-α-tetralone
is used in place of the 2-bromo-α-tetralone above there is obtained a. 3'-(4-pyridyl)-spiro[6-chloro-1,2,3,4-tetrahydronaphthalene-2,2'-oxirane]-1-one;
  b. 3'-(4-pyridyl)-spiro[6-methyl-1,2,3,4-tetrahydronaphthalene-2,2'-oxirane]-1-one;
  c. 3'-(4-pyridyl)-spiro[6,7-dimethoxy-1,2,3,4-tetrahydronaphthalene12,2'-oxirane]-1-one;
  d. 3'-(4-pyridyl)-spiro[6-trifluoromethyl-1,2,3,4-tetrahydronaphthalene-2,2'-oxirane]-1-one or
  e. 3'-(4-pyridyl)-spiro[6,7-methylenedioxy-1,2,3,4-tetrahydronaphalene-2,2'-oxirane]-1-one respectively.

When an equivalent amount of
f. 2-thiophenealdehyde;
g. 2-furfural;
h. p-tolualdehyde
i. m-trifluoromethylbenzaldehyde
j. 3,4-methylenedioxybenzaldehyde
k. p-chlorobenzaldehyde or
l. p-methoxybenzaldehyde
is used in place of the pyridine-4-carboxyaldehyde above, there is obtained f. 3'-(2-thienyl)-spiro[1,2,3,4-tetrahydronaphthalene-2,2'-oxirane]-1-one;
  g. 3'-(2-furyl)-spiro[1,2,3,4-tetrahydronaphthalene-2,2'-oxirane]-1-one;
  h. 3'-(p-toxyl)-spiro[1,2,3,4-tetrahydronaphthalene-2,2-oxirane]-1-one;
  i. 3'-(m-trifluoromethylphenyl)-spiro[1,2,3,4-tetrahydronaphthalene-2,2'-oxirane]-1-one;
  j. 3'-(3,4-methyledioxyphenyl)-spiro[1,2,3,4-tetrahydronaphthalene-2,2'-oxirane]-1-one;
  k. 3'-(p-chlorophenyl)-spiro[1,2,3,4-tetrahydronaphthalene-2,2'-oxirane]-1-one or
  l. 3'-(p-methoxyphenyl)-spiro[1,2,3,4-tetrahydronaphthlene-2,2'-oxirane]-1-one respectively.

Step B:
4,5-dihydro-3-(4-pyridyl)-2H-naphtho[1,2-c]pyrazole

Three grams of 3'-(4-pyridyl)-spiro[1,2,3,4-tetrahydronaphthalene-2,2'-oxirane]-1-one in 10 ml. of ethyl alcohol is added to 18 ml of 98% hydrazine, 3.5 ml. of acetic acid and 12 ml of dioxane and refluxed for 12 hours. On cooling the mixture, 4,5-dihydro-3-(4-pyridyl)-2H-naphtho[1,2-c]pyrazole precipitates and is recovered by filtration (m.p. of base 229°C; m.p. of hydrochloride salt >300°C).

Following the above procedure but using an equivalent amount of
a. 3'-(4-pyridyl)-spiro[6-chloro-1,2,3,4-tetrahydronaphthalene-2,2'-oxirane]-1-one;
b. 3'-(4-pyridyl)-spiro[6-methyl-1,2,3,4-tetrahydronaphthalene-2,2'-oxirane]-1-one;
c. 3'-(4-pyridyl)-spiro[6,7-dimethoxy-1,2,3,4-tetrahydronaphthalene-2,2'-oxirane]-1-one;
d. 3'-(4-pyridyl)-spiro[6-trifluoromethyl-1,2,3,4-tetrahydronaphthalene-2,2'-oxirane]-1-one;
e. 3'-(4-pyridyl)-spiro[6,7-methylenedioxy-1,2,3,4-tetrahydronaphthalene-2,2'-oxirane]-1-one;
f. 3'-(2-thienyl)-spiro[1,2,3,4-tetrahydronaphthalene-2,2'-oxirane]-1-one;
g. 3'-(2-furyl)-spiro[1,2,3,4-tetrahydronaphthalene-2,2'-oxirane]-1-one;
h. 3'-(p-tolyl)-spiro[1,2,3,4-tetrahydronaphthalene-2,2'-oxirane]-1-one;
i. 3'-(m-trifluoromethylphenyl)-spiro[1,2,3,4-tetrahydronaphthalene-2,2'-oxirane]-1-one;
j. 3'-(3,4-methylenedioxyphenyl)-spiro[1,2,3,4-tetrahydronaphthalene-2,2'-oxirane]-1-one;
k. 3'-(p-chlorophenyl)-spiro[1,2,3,4-tetrahydronaphthalene-2,2'-oxirane]-1-one or
l. 3'-(p-methoxyphenyl)-spiro[1,2,3,4-tetrahydronaphthalene-2,2'-oxirane]-1-one in place of the 3'-(4-pyridyl)-spiro[1,2,3,4-tetrahydronaphthalene-2,2'-oxirane]-1-one used therein there is obtained
a. 7-chloro-4,5-dihydro-3-(4-pyridyl)-2H-naphtho[1,2-c]pyrazole;
b. 7-methyl-4,5-dihydro-3-(4-pyridyl)-2H-naphtho[1,2-c]pyrazole;
c. 7,8-dimethoxy-4,5-dihydro-3-(4-pyridyl)-2H-naphtho[1,2-c]pyrazole;
d. 7-trifluoromethyl-4,5-dihydro-3-(4-pyridyl)-2H-naphtho[1,2-c]pyrazole;
e. 7,8-methylenedioxy-4,5-dihydro-3-(4-pyridyl)-2H-naphtho[1,2-c]pyrazole;
f. 4,5-dihydro-3-(2-thienyl)-2H-naphtho[1,2-c]pyrazole;
g. 4,5-dihydro-3-(2-furyl)-2H-naphtho[1,2-c]pyrazole;
h. 4,5-dihydro-3-(p-tolyl)-2H-naphtho[1,2-c]pyrazole;
i. 4,5-dihydro-3-(m-trifluoromethylphenyl)-2H-naphtho[1,2-c]pyrazole;
j. 4,5-dihydro-3-(3,4-methylendioxyphenyl)-2H-naphtho[1,2-c]pyrazole;
k. 4,5-dihydro-3-(p-chlorophenyl)-2H-naphtho[1,2-c]pyrazole (m.p. 194°–195°C) or
l. 4,5-dihydro-3-(p-methoxyphenyl)-2H-naphtho[1,2-c]pyrazole(m.p. 161°–163°C) respectively.

Step C: 3-(4-pyridyl)-2H-naphtho[1,2-c]pyrazole

A mixture of 6.0 grams of 4,5-dihydro-3-(4-pyridyl)-2H-naphtho [1,2-c]pyrazole, 6.0 grams of 5% palladium or carbon, 150 ml of absolute ethanol and 50 ml of dry dioxane are stired and refluxed for about 75 hours. The mixture is allowed to cool to room temperature, and is then treated with about 50 ml of 1:1 methanol/methylene dichloride. The mixture is stirred for about 15 minutes and then filtered through celite. The filtrate is concentrated in vacuo and the residue crystallized from ethanol/ether to give 3-(4-pyridyl)-2H-naphtho[1,2-c]pyrazole, (m.p. 273°–276°.)

The 3-(4-pyridyl)-2H-naphtho[1,2-c]pyrazole of this example is an effective anti-fertility agent when administered to a female mammal at a dosage of 25 milligrams 2 to 4 times a day.

When the above procedure is carried out using an equivalent amount of
a. 7-chloro-4,5-dihydro-3-(4-pyridyl)-2H-naphtho[1,2-c]pyrazole;
b. 7-methyl-4,5-dihydro-3-(4-pyridyl)-2H-naphtho[1,2-c]pyrazole;
c. 7,8-dimethoxy-4,5-dihydro-3-(4-pyridyl)-2H-naphtho[1,2-c]pyrazole;
d. 7-trifluoromethyl-4,5-dihydro-3-(4-pyridyl)-2H-naphtho[1,2-c]pyrazole;
e. 7,8-methylenedioxy-4,5-dihydro-3-(4-pyridyl)-2H-naphtho[1,2-c]pyrazole;
f. 4,5-dihydro-3-(2-thienyl)-2H-naphtho[1,2-c]pyrazole;
g. 4,5-dihydro-3-(2-furyl)-2H-naphtho[1,2-c]pyrazole;
h. 4,5-dihydro-3-(p-tolyl)-2H-naphtho[1,2-c]pyrazole;
i. 4,5-dihydro-3-(m-trifluoromethylphenyl)-2H-naphtho[1,2-c]pyrazole;
j. 4,5-dihydro-3-(3,4-methylenedioxyphenyl)-2H-naphtho[1,2-c]pyrazole;
k. 4,5-dihydro-3-(p-chlorophenyl)-2H-naphtho[1,2-c]pyrazole or
l. 4,5-dihydro-3-(p-methoxyphenyl)-2H-naphtho[1,2-c]pyrazole (m.p. 161°–163°C), in place of the 4,5-dihydro-3-(4-pyridyl)2H-naphtho[1,2-c]pyrazole, there is obtained
a. 7-chloro-3-(4-pyridyl)-2H-naphtho[1,2-c]pyrazole;
b. 7-methyl-3-(4-pyridyl)-2H-naphtho[1,2-c]pyrazole;
c. 7,8-dimethoxy-3-(4-pyridyl)-2H-naphtho[1,2-c]pyrazole;
d. 7-trifluoromethyl-3-(4-pyridyl)-2H-naphtho[1,2-c]pyrazole;
e. 7,8-methylenedioxy-3-(4-pyridyl)-2H-naphtho[1,2-c]pyrazole;
f. 3-(2-thienyl)-2H-naphtho[1,2-c]pyrazole;
g. 3-(2-furyl)-2H-naphtho[1,2-c]pyrazole;
h. 3-(p-tolyl)-2H-naphtho[1,2-c]pyrazole;
i. 3-(m-trifluoromethylphenyl)-2H-naphtho[1,2-c]pyrazole;
j. 3-(3,4-methylenedioxyphenyl)-2H-naphtho[1,2-c]pyrazole;
k. 3-(p-chlorophenyl)-2H-naphtho[1,2-c]pyrazole, or
l. 3-(p-methoxyphenyl)-2H-naphtho[1,2-c]pyrazole respectively

EXAMPLE 2

3-(4-pyridyl)-2H-naphtho[1,2-c]pyrazole

A solution of 10 grams of 2-(1-hydroxynaphthyl)-4-pyridyl ketone in 200 ml of diethylene glycol is treated with 10 ml. of 97% hydrazine. The solution is blanketed with nitrogen and refluxed for 3 hours. The reaction mixture is then concentrated in vacuo to about one fifth the original volume and treated with about 200 ml. of cold water. The resultant solid is filtered off and crystallized from 95% ethanol to give 3-(4-pyridyl)-2H-naphtho[1,2-c]pyrazole m.p. 271°–273°.

When the above process is carried out using an equivalent amount of
a. 2-(6-chloro-1-hydroxynaphthyl)-4-pyridyl ketone;
b. 2-(6-methyl-1-hydroxynaphthyl)-4-pyridyl ketone;
c. 2-(6,7-dimethoxy-1-hydroxynaphthyl)-4-pyridyl ketone;
d. 2-(6-trifluoromethyl-1-hydroxynaphthyl)-4-pyridyl ketone;
e. 2-(6,7-methylenedioxy-1-hydroxynaphthyl)-4-pyridyl ketone;
f. 2-(1-hydroxynaphthyl)-2-thienyl ketone;
g. 2-(1-hydroxynaphthyl)-2-furyl ketone;
h. 2-(1-hydroxynaphthyl)-4-tolyl ketone;
i. 2-(1-hydroxynaphthyl)-3-trifluoromethylphenyl ketone;
j. 2-(1-hydroxynaphthyl)-3,4-methylenedioxyphenyl ketone;
k. 2-(1-hydroxynaphthyl)-4-chlorophenyl ketone or
l. 2-(1-hydroxynaphthyl)-4-metoxyphenyl ketone
in place of the 2-(1-hydroxynaphthyl)-4-pyridyl ketone, there is obtained
a. 7-chloro-3-(4-pyridyl)-2H-naphtho[1,2-c]pyrazole;
b. 7-methyl-3-(4-pyridyl)-2H-naphtho[1,2-c]pyrazole;
c. 7,8-dimethoxy-3-(4-pyridyl)-2H-naphtho[1,2-c]pyrazole;
d. 7-trifluoromethyl-3-(4-pyridyl)-2H-naphtho[1,2-c]pyrazole;
e. 7,8-methylenedioxy-3-(4-pyridyl)-2H-naphtho[1,2-c]pyrazole;
f. 3-(2-thienyl)-2H-naphtho[1,2-c]pyrazole;
g. 3-(2-furyl)-2H-naphtho[1,2-c]pyrazole;
h. 3-(p-tolyl)-2H-naphtho[1,2-c]pyrazole;
i. 3-(m-trifluoromethylphenyl)-2H-naphtho[1,2-c]pyrazole;
j. 3-(3,4-methylenedioxyphenyl)-2H-naphtho[1,2-c]pyrazole;
k. 3-(p-chlorophenyl)-2H-naphtho[1,2-c]pyrazole, or
l. 3-(p-methoxyphenyl)-2H-naphtho[1,2-c]pyrazole respectively.

EXAMPLE 3

A solution of 16 grams (0.10 mole) of 1-naphthyl hydrazine, 15.1 grams (0.10 moles) of ethyl isonicotinate and 300 ml. of isopropanol are stirred and refluxed for 48 hours. The solvent is removed in vacuo and the resultant 2-(1-naphthyl)-isonicotinic acid hydrazide is added to 125 ml. of phosphorous oxychloride and stirred and refluxed for about 15 hours. The reaction mixture is then concentrated in vacuo and the resultant simi-solid dissolved in about 250 ml. methylene dichloride. The methylene dichloride layer is washed with 100 ml of cold 2N potassium hydroxide, 100 ml. of water, dried with magnesium sulfate, filtered and concentrated in vacuo. Crystallization from ethanol/ether yields 3-(4-pyridyl)-2H-naphtho[1,2-c]pyrazole, m.p. 271°–273°.

When the above process is carried out using a equivalent amount of
a. 6-chloro-1-naphthyl hydrazine
b. 6-methyl-1-naphthyl hydrazine
c. 6,7-dimethoxy-1-naphthyl hydrazine
d. 6-trifluoromethyl-1-naphthyl hydrazine or
e. 6,7-methylenedioxy-1-naphthyl hydrazine
in place of the 1-naphthyl hydrazine there is obtaind
a. 7-chloro-3-(4-pyridyl)-2H-naphtho[1,2-c]pyrazole;
b. 7-methyl-3-(4-pyridyl)-2H-naphtho[1,2-c]pyrazole;
c. 7,8-dimethoxy-3-(4-pyridyl)-2H-naphtho[1,2-c]pyrazole;
d. 7-trifluoromethyl-3-(4-pyridyl)-2H-naphtho[1,2-c]pyrazole, or
e. 7,8-methylenedioxy-3-(4-pyridyl)-2H-naphtho[1,2-c]-yrazole, respectively.

Following the above procedure, but using an equivalent amount of
f. 2-thienyl carboxylic acid, ethyl ester;
g. 2-furyl carboxylic acid, ethyl ester;
h. p-toluic acid, ethyl ester;
i. m-trifluoromethylbenzoic acid, ethyl ester;
j. 3,4-methylenedioxybenzoic acid, ethyl ester;
k. p-chlorobenzoic acid, ethyl ester or
l. p-methoxybenzoic acid, ethyl ester in place of the ethyl isonicotinate there is obtained
f. 3-(2-thienyl)-2H-naphtho[1,2-c]pyrazole;
g. 3-(2-furyl)-2H-naphtho[1,2-c]pyrazole;
h. 3-(p-tolyl)-2H-naphtho[1,2-c]pyrazole;
i. 3-(m-trifluoromethylphenyl)-2H-naphtho[1,2-c]pyrazole;
j. 3-(3,4-methylenedioxyphenyl)-2H-naphtho[1,2-c]pyrazole;
k. 3-(p-chlorophenyl)-2H-naphtho[1,2-]pyrazole, or
l. 3-(p-methoxyphenyl)-2H-naphtho[1,2-c]pyrazole respectively.

What is claimed is:
1. A compound of the formula

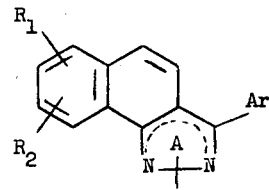

where ring A represents the structures

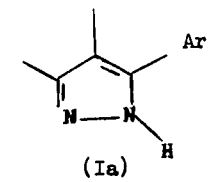 or 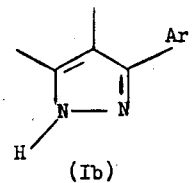

Ar is

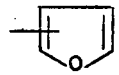

2. The compound according to claim 1, which is 3-(2-furyl)-2H-naphtho[1,2-c]pyrazole.
3. The compound which is 3-(p-methoxyphenyl)-2H-naphtho[1,2-c]pyrazole.

* * * * *